United States Patent [19]
Fossel et al.

[11] Patent Number: 5,217,716
[45] Date of Patent: Jun. 8, 1993

[54] METHOD FOR TREATING VIRAL INFECTIONS USING OXIDIZED LIPOPROTEINS

[75] Inventors: Eric T. Fossel, Chestnut Hill; James E. Lyddy, Arlington, both of Mass.

[73] Assignee: The Beth Israel Hospital Association, Boston, Mass.

[21] Appl. No.: 776,690

[22] Filed: Oct. 15, 1991

Related U.S. Application Data

[63] Continuation of Ser. No. 554,807, Jul. 18, 1990, abandoned.

[51] Int. Cl.$^5$ .................. A61K 37/00; A61K 37/50; C07K 3/00
[52] U.S. Cl. .................. 424/94.4; 530/830; 530/359; 514/21
[58] Field of Search .................. 514/21, 78; 424/94.4; 530/830, 359

[56] References Cited

PUBLICATIONS

Hessler, et al. Arteriosclerosis vol. 3 n 3, May/Jun. 1983 pp. 215-222.
Marel, et al. J. of Lipid Research vol. 24 v 24, 1983 pp. 1070-1078.

Primary Examiner—Douglas W. Robinson
Assistant Examiner—Jane A. Williams
Attorney, Agent, or Firm—Lorusso & Loud

[57] ABSTRACT

This invention provides methods and an apparatus for peroxidizing lipoproteins and introducing them into a person infected with a virus such as HIV to help that person fight the disease. Peroxidized low density lipoproteins are shown to preferentially kill HIV-infected cells as well as the HIV virus.

3 Claims, 2 Drawing Sheets

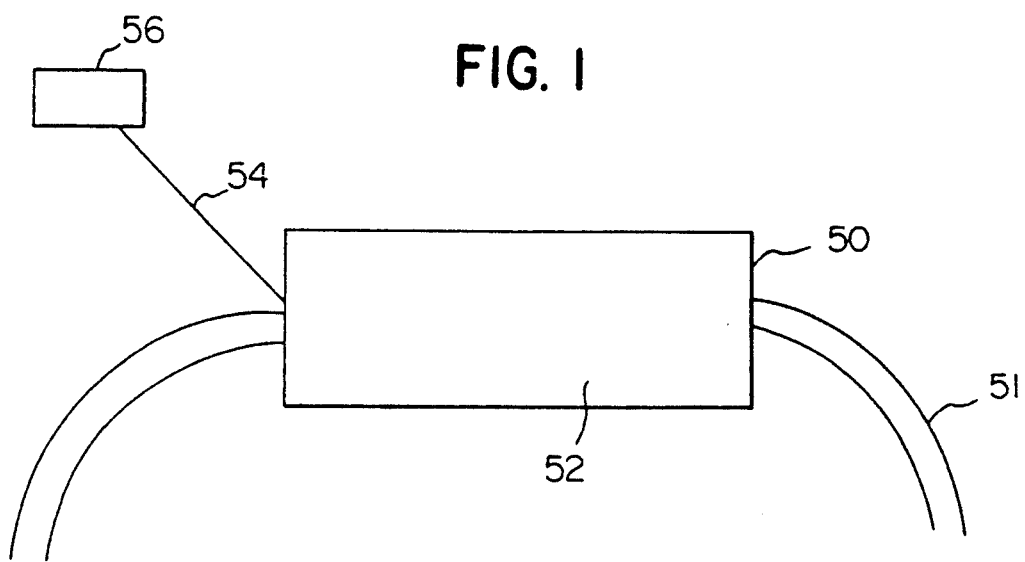
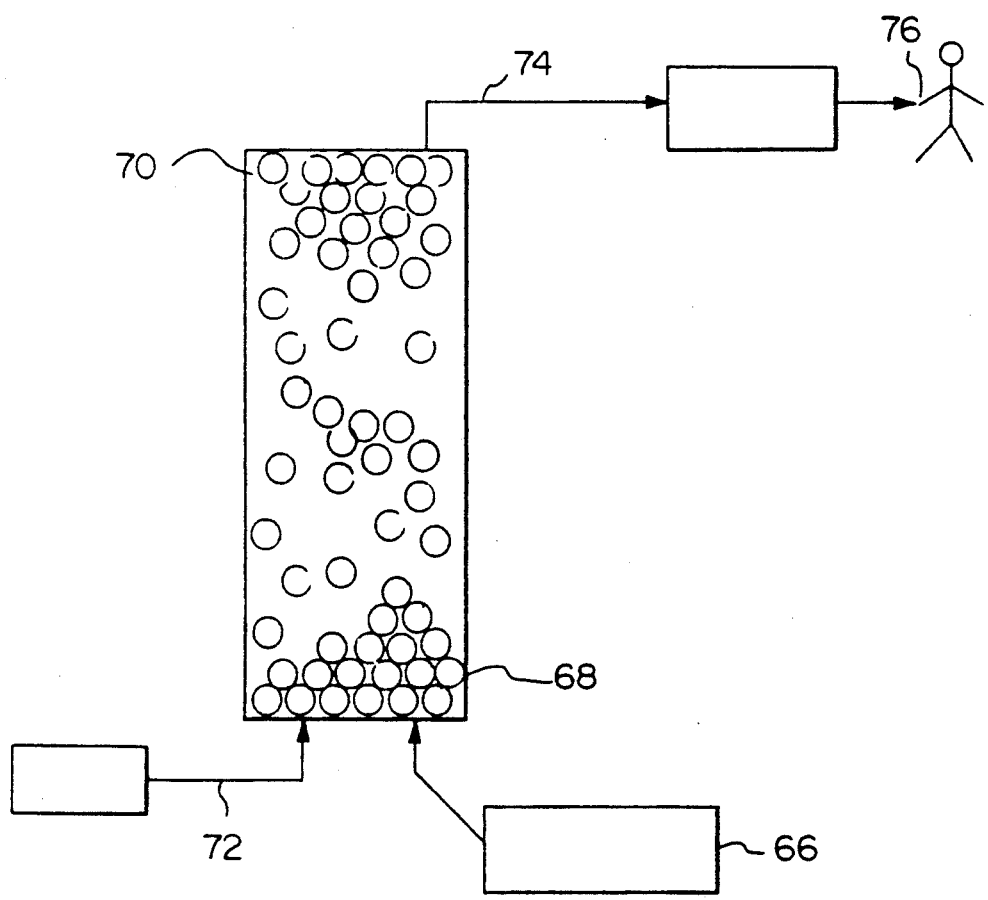

METHOD FOR TREATING VIRAL INFECTIONS USING OXIDIZED LIPOPROTEINS

BACKGROUND OF THE INVENTION

Statement Regarding Federally Sponsored Research

Funding for work described herein was provided by the Federal Government under a grant from the Department of Health and Human Services. The Government may have certain rights in this invention.

This is a continuation of copending application Ser. No. 07/554,807, filed on Jul. 18, 1990, now abandoned.

This invention relates to treating viral infections and particularly Acquired Immunodeficiency Syndrome (AIDS) in a living patient using oxidized lipoproteins, preferably peroxidized low density lipoproteins (p-LDL). Lipoproteins as a group include chylomicrons, chylomicron remnants, very low density lipoproteins, intermediate density lipoproteins, low density lipoproteins and high density lipoproteins. All of these can serve as a source of oxidized lipoproteins. More particularly, this invention relates to a method and an apparatus for producing and administering effective doses of oxidized lipoproteins into a patient's bloodstream in order to kill the Human Immunodeficiency Virus (HIV) and HIV-infected cells, leaving most healthy cells intact.

Extensive literature exists o the cytotoxicity of the products of lipid oxidation and peroxidation. For the most part, these prior studies have focused on oxidation products of a particular lipid, often linoleic acid. It is well known, that hydrogen peroxide itself is toxic to virtually all cell types. More recently, several workers have focused attention on the cytotoxicity of the polyunsaturated fatty acid peroxidation products.

Since oxidized lipids are cytotoxic to a majority of cell types, it is therefore desirable to find an agent which will be effective against viruses such as HIV and which will preferentially target virus-infected Cells, particularly HIV-infected cells. The lipoprotein chosen must be one that the viruses and/or diseased cells have an enhanced ability, compared to normal cells of similar type, to take up or transport across their membranes. Also, the lipoprotein must be capable of being oxidized and preferably peroxidized with hydrogen peroxide.

SUMMARY OF THE INVENTION

In accordance with the present invention, it was discovered that virus-infected cells are more susceptible than healthy cells to the cytotoxic effect of oxidized lipoproteins as defined herein. It was also discovered that p-LDL kills the virus as well. The mechanism by which this preferential cytotoxicity occurs is not understood. It appears, that viruses and virus-infected cells have an enhanced ability to take up lipoproteins or an enhanced ability to transport lipoproteins across their membranes or an increased susceptibility to oxidized lipoproteins. Some diseased cells may take up more oxidized lipoproteins through an increased number of lipoprotein receptors. However, we are not aware of any evidence that viruses or virus-infected cells have been demonstrated to have an increased number of lipoprotein receptors.

Examples of viruses and virus infections that may be treated by the administration of oxidized lipoproteins include retroviruses including HIV, hepatitis, cytomegalovirus, herpes, pneumonia, varicella zooster virus, influenza virus and others.

One important method for treating viral infections such as AIDS, with peroxidized lipoproteins, involves administering p-LDL directly to the patient. Such administration may be accomplished by introducing p-LDL enriched blood directly into a patient's blood stream.

Hydrogen peroxide or organic peroxides are capable of generating free-radicals which in turn can peroxidize LDL to kill the virus or virus-containing cells. Thus, a second method for treating viral infections, such as AIDS, using oxidized lipoproteins comprises introducing a therapeutic dose of organic peroxide into a diseased patient which makes p-LDL more cytotoxic to diseased cells infected with the virus. Administering non-oxidized but modified LDL should enhance the effect of the organic peroxides. Modified LDL is prepared by enriching the content of natural LDL with specific triglycerides, phospholipids, or cholesterol esters which are more easily oxidized or which result in more cytotoxic peroxidation products.

A third method for producing peroxidized lipoproteins involves subjecting blood fluid lipids directly to hydrogen peroxide or organic peroxides alone or in the presence of an enzyme such as peroxidase. An apparatus for accomplishing the latter method comprises an extracorporeal module for installation in an AV (atrioventricular) shunt or arterial bypass, which includes a peroxidizing module and an inlet from a means, such as a pump, which can slowly and precisely introduce a flow of peroxide. Utilizing blood as a source of oxidized low density lipoproteins is a very important embodiment of the present invention. This embodiment has many variations. For example, in its simplest embodiment, blood is removed from a patient and treated under peroxidizing conditions to oxidize or peroxidize the lipoproteins present in the blood. The blood Can be monitored for oxidized lipoprotein level by proton and carbon-13 nuclear magnetic resonance (NMR) spectroscopy and returned to the patient where the oxidized lipoproteins will come in contact with high metabolism virus infected cells, where the peroxidized lipoprotein will be taken up by such cells and the cells will be killed. Also, a patient's blood or blood from a donor source can be treated as described above, but in addition, the blood can be enriched with lipoproteins from other sources and then oxidized. Furthermore, an agent known to increase a cell's uptake of lipoproteins can be administered to the patient as pretreatment in addition to further enriching the blood with a peroxide. Thus, in the latter embodiment, a patient can receive blood from a donor which is superenriched with oxidized lipoproteins, which contains an agent to increase the virus or virus-infected cell's ability to take up such lipoproteins and which further contains an oxidant to oxidize those lipoproteins already present in the patient.

The lipid oxidation processes of the body may be further augmented by increasing the oxygen level in the blood via inhalation of increased levels of elemental oxygen during breathing. Perfluorocarbon fluosal may also be used to increase the oxygen level in the blood.

Accordingly, it is an object of the present invention to provide a chemotherapeutic method of acceptable toxicity for fighting viral infections such as AIDS such diseases being characterized by virus or infected cells with an enhanced ability to take up lipoproteins.

It is a further object of the present invention to help the patient fight viral infections such as AIDS by increasing the level of oxidized lipoproteins taken up by infected cells.

It is another object of the present invention to use p-LDL, whose presence can be easily monitored using NMR spectroscopy, to fight viral infections such as AIDS in a patient.

It is yet another object of the present invention to provide a method and an apparatus for peroxidizing lipoproteins in the blood of a virus infected patient to produce a therapeutic source of p-LDL.

Other objects and advantages of the invention will become apparent from the description of the invention which follows made with reference to the drawings.

BRIEF DESCRIPTION OF THE DRAWINGS

FIG. 1 shows the apparatus of the invention where by means of an extracorporeal peroxidizing module, a patient's lipoproteins are peroxidized directly;

FIG. 5 shows an apparatus for oxidizing the lipoproteins in a blood supply.

DETAILED DESCRIPTION OF THE PREFERRED EMBODIMENTS

Figure 2:
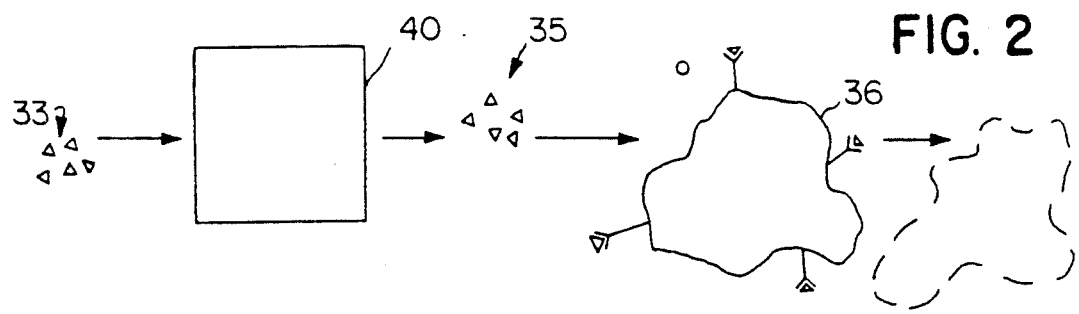
FIG. 2 is a schematic diagram of the general method for using p-LDL cytotoxicity to treat virus infections in humans in accordance with the claimed invention.

At the outset, the invention is described in its broadest overall aspects, with a more detailed description following. In its broadest overall aspects, this invention is a method of treating virus infections such as AIDS which is a disease state characterized by the presence of diseased cells with an enhanced ability to take up lipoproteins or an increased susceptibility to oxidized lipoproteins. The treatment consists of the absorption of oxidized lipoproteins, preferably peroxidized low density lipoproteins, by viruses or infected cells with an enhanced ability to take up lipoproteins. Likewise, it is recognized that virus relies on its host cell for viability. In accordance with the present invention, it has been discovered that oxidized or peroxidized lipoproteins will preferentially kill virus-infected cells such as HIV-infected cells. Thus, the present invention is directed to methods and apparatus for the purpose of increasing the likelihood that oxidized lipoproteins will be taken up by virus-infected cells in order to destroy such cells.

The effect of oxidized LDL on HIV-infected cells was tested in an independent laboratory with the following results. CR10 cells chronically infected with HIV-1/NIT virus and Phytohemagglutinin stimulated cultured peripheral blood mononuclear cells from individuals negative for HIV-1 antibody were incubated with an oxidized form of LDL. After 48 hours of incubation, exclusion assays were performed to determine cell survival following treatment with LDL. The Trypan Blue Exclusion assay results show that oxidized LDL has a selectively toxic effect on HIV-1 infected cells. See Table I below for specific test results.

TABLE I

| | Viability as Determined by Trypan Blue Exclusion | | |
|---|---|---|---|
| Day | Treatment | Uninfected cells | Infected cells |
| 0 | untreated | 89% | 90% |
| 2 | untreated | 89% | 87% |
| 2 | W/1:1000 p-LDL | 75% | 16% |

Whereas the above results have demonstrated that p-LDL is preferentially cytotoxic to HIV-infected cells, the results in Table II show that p-LDL treatment kills the HIV virsus as well.

TABLE II

| HIV Antigen Endpoint Titration Results | | | |
|---|---|---|---|
| p-LDL Dilution | CR10 Infected/ Treated Day 2 | p-LDL Dilution | CR10 Infected/ Untreated Day 2 |
| 1:10 | 1:16 | Untreated | 1:64 |
| 1:100 | 1:32 | | |
| 1:1000 | 1:32 | | |
| 1:10,000 | 1:32 | | |
| 1:100,000 | 1:32 | | |

Table II shows the titration results for HIV-1 antigen in CR10 culture supernatant fluids at Day 2 of treatment. This antibody-antigen precipitation experiment is designed using a titration dilution. In the infected and untreated controls the titration ratio was carried out to 1:64 to eliminate the antibody-antigen response. In the supernatant for the infected and treated cells, the titration ratio only needed to reach 1:16 for p-LDL dilution of 1:10 and 1:32 for more dilute p-LDL.

This experiment demonstrates that the HIV virus was less viable after treatment in comparison with controls. It is not yet known whether p-LDL directly killed the virus or whether p-LDL killed the host cell without which the virus cannot live, or both.

Lipoproteins circulating in the blood take various forms including chylomicrons, chylomicron remnants, very low density lipoproteins, intermediate density lipoproteins, low density lipoproteins, and high density lipoproteins. Certain lipids associate with specific proteins to form lipid/protein systems in which the specific physical properties of these two classes of biomolecules are blended. There are two major types, transport lipoproteins and membrane systems. In the membrane systems, the lipids and proteins ar not covalently joined but are held together largely by hydrophobic interactions between the nonpolar portions of the lipid and the protein components.

The plasma transport lipoproteins are complexes in which the lipids and proteins occur in a relatively fixed ratio. They carry water-insoluble lipids between various organs via blood, in a form with a relatively small and constant particle diameter and weight. Human plasma lipoproteins occur in four major classes that differ in density as well as particle size as shown in the table below.

TABLE III

| | Major Classes of Human Plasma Lipoproteins | | | |
|---|---|---|---|---|
| | Chylomicrons | Very low density lipoproteins (VLDL) | Low-density lipoproteins (LDL) | High-density lipoproteins (HDL) |
| Density, g ml$^{-1}$ | <0.94 | 0.94–1.006 | 1.006–1.063 | 1.063–1.21 |
| Flotation rate, $S_1$ | >400 | 20–400 | 0–20 | (Sediment) |
| Particle size, nm | 75–1,000 | 30–50 | 20–22 | 7.5–10 |

TABLE III-continued

| Major Classes of Human Plasma Lipoproteins | | | | |
|---|---|---|---|---|
| | Chylomicrons | Very low density lipoproteins (VLDL) | Low-density lipoproteins (LDL) | High-density lipoproteins (HDL) |
| Protein, % of dry weight | 1–2 | 10 | 25 | 45–55 |
| Triacylglycerols, % of dry weight | 80–95 | 55–65 | 10 | 3 |
| Phospholipids, % of dry weight | 3–6 | 15–20 | 22 | 30 |
| Cholesterol, free, % of dry weight | 1–3 | 10 | 8 | 3 |
| Cholesterol, esterified, % of dry weight | 2–4 | 5 | 37 | 15 |

There are pathways within the body for interconversion among the four major classes. Thus, any of the four classes can be administered but it has been found that the peroxidized low density lipoproteins that ar the most effective.

As shown in the above table, the plasma lipoproteins contain varying proportions of protein and different types of lipid. The very low-density lipoproteins contain four different type of polypeptide chains having distinctive amino acid sequences. The high-density lipoproteins have two different types of polypeptide chains, of molecular weight 17,500 and 28,000. The polypeptide chains of the plasma lipoproteins are believed to be arranged o the surface of the molecules, thus conferring hydrophilic properLies. However, in the very low-density lipoproteins and chylomicrons, there is insufficient protein to cover the surface; presumably the polar heads of the phospholipid components also contribute hydrophilic groups on the surface, with the nonpolar triacylglycerols in the interior. *Biochemistry*, Lehninger, Worth Publishers, Inc., New York, 1975, pp. 301.

When low density lipoproteins (LDL) are oxidized, they have a preferential cytotoxic effect on virus-infected cells such as HIV-infected cells, which have an enhanced ability to take-up lipoproteins.

An important factor in selecting a lipoprotein for killing virus-infected cells according to the present invention is that the lipoprotein chosen be one which the diseased cells have an enhanced ability to take-up or transport across their membrane or to which they have an increased susceptibility. Another important characteristic of the lipoprotein is that it be capable of being oxidized, preferably peroxidized by reaction with hydrogen peroxide.

Although it is believed that the oxidation of lipoproteins according to the present invention produces a new class of substances, the chemistry for oxidizing lipoproteins is readily apparent from analyzing the prior art. In this regard, the procedures and techniques for oxidizing lipids are well documented. According to the most preferred embodiment of the present invention lipoproteins are oxidized by reaction with horseradish peroxidase and hydrogen peroxide.

Accordingly, one method of the present invention for treating virus infections such as AIDS, a disease state characterized by diseased cells with an enhanced ability to take-up lipoproteins or an increased susceptibility to oxidized lipoproteins, using p-LDL, is as follows. Therapeutic doses of an oxidant, such as an organic peroxide, or more specifically such as ditertiarybutyl peroxide are introduced into patients diagnosed as having a viral infection such as AIDS by methods well known in the art. The progress of the disease is monitored by conventional methods and the organic peroxide dose adjusted accordingly. Administering modified lipoproteins should enhance the effect of these peroxides. Modified lipoproteins are prepared by enriching the content of natural lipoproteins with specific triglycerides, phospholipids, or cholesterol esters. Other enzymes and oxidants such as flavins and riboflavin and oxidases such as peroxidase and lipoxidase may also be used in this embodiment.

In a second embodiment, the lipoproteins in a patient's blood are peroxidized directly by the method and apparatus of the invention. The apparatus consists of an extracorporeal peroxidizing module 50 (FIG. 1) which is installed through an A-V shunt or arterial bypass 51. The module 50 includes an immobilized enzyme 52 such as peroxidase or lipoxidase and an inlet 54 from a pump 56 which can very slowly and precisely introduce a flow of hydrogen peroxide into the blood.

The lipid peroxidation process of the body may be further augmented by increasing the oxygen level in the blood via inhalation of increased levels of elemental oxygen during breathing. Perfluorocarbon fluosal may also be used to increase the oxygen level in the blood.

In a third embodiment, patients with virus infections such as AIDS, a disease state characterized by diseased cells with an enhanced ability to take up lipoproteins or an increased susceptibility to oxidized lipoproteins, are treated by direct administration of peroxidized lipoproteins. Peroxidized low density lipoproteins produce the best results.

Referring now to FIG. 2 where the general method for using p-LDL cytotoxicity to treat virus infections, such as AIDS in humans, is shown. According to the method of this invention, LDL 33 will be converted directly to p-LDL 35 by exposure to a chemical agent 40 as described below. In one embodiment, the agent 40 is ditertiarybutyl peroxide. In a second embodiment, the agent 40 is peroxidase together with peroxide. HIV-infected cells 36 will die in preference to normal cells.

Figure 3:
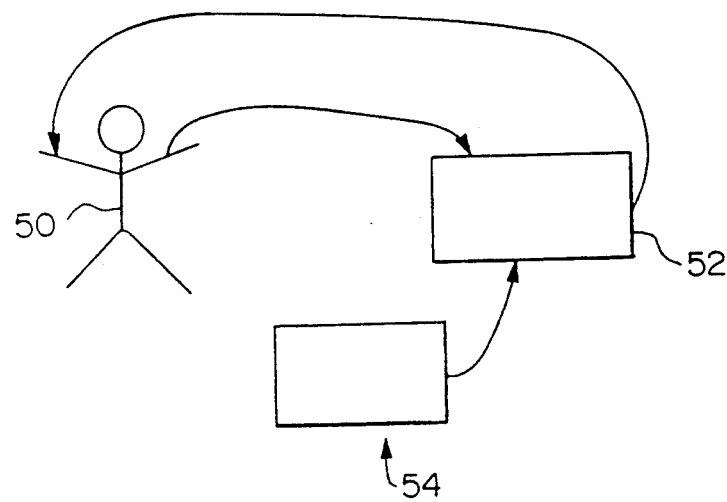
FIG. 3 shows a procedure and apparatus for oxidizing the lipoproteins of a patient.

FIG. 3 depicts another embodiment of this invention in which blood is transferred from a patient 50 to a container 52 the interior walls of which are coated with an immobilized enzyme such as a lipoxidase or a peroxidase such as horseradish peroxidase. A peroxide 54 is added to the container resulting in the formation of oxidized lipoproteins which are then transferred back to the patient 50.

Figure 4:
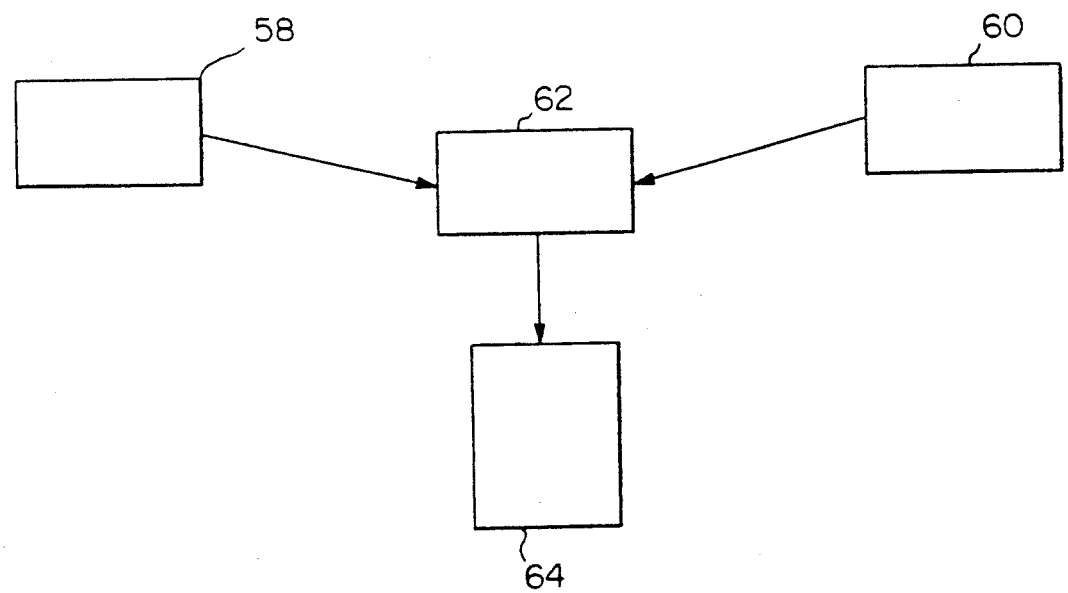
FIG. 4 shows an apparatus for oxidizing the lipoproteins in a blood supply.

FIG. 4 depicts still another embodiment of this invention wherein a blood supply 58 is secured. It may be from a patient, a donor or any other compatible blood source. The blood 58 and an oxidant 60, such as hydrogen peroxide, are introduced into a container 62 thus forming oxidized lipoproteins. The oxidized lipoprotein-containing blood is then transferred to a storage container 64 until needed for treatment.

The present invention is further illustrated by the following nonlimiting examples.

EXAMPLE 1

Once a patient is diagnosed as having a virus infection, such as AIDS by methods well known in the art, peroxidized lipoproteins are injected intravenously. The progress of the HIV infection is monitored by conventional methods and the peroxidized low density lipoprotein dose is adjusted accordingly. The extent of lipid peroxidation is measured by performing a proton and carbon-13 (128/130 ppm ratio) NMR analysis of the oxidized low density lipoprotein solution.

EXAMPLE 2

Once a patient is diagnosed as having AIDS or believed to be at risk for AIDS, by methods well known in the art, peroxidized low density lipoproteins are administered orally or intravenously. The progress of the HIV infection is monitored by conventional methods and the peroxidized low density lipoprotein dose is adjusted accordingly.

EXAMPLE 3

Once a patient is diagnosed as having AIDS or believed to be at risk for AIDS, by methods well known in the art. ditertiarybutyl peroxide is administered by i.v. (intravenous) injection. The progress of the HIV infection is monitored by conventional methods and the ditertiarybutyl peroxide dose adjusted accordingly.

The patient's blood oxygen supply may also be augmented by inhalation of elemental oxygen or by i.v. injection of perfluorocarbon fluosal.

Additionally, the patient's supply of lipoproteins may be augmented by intravenous injection of lipoproteins enriched with triglycerides, phospholipids or cholesterol esters.

The ditertiarybutyl peroxide of this procedure may be replaced with any of the following in its proper dose: riboflavin, peroxidase, lipoxidase or other flavins, peroxides, organic peroxides or oxidases. The extent of lipid peroxidation is measured by performing a proton and carbon-13 (128/130 ppm ratio) NMR analysis of the oxidized low density lipoprotein-containing blood.

EXAMPLE 4

Once a patient is diagnosed or suspected as having a viral infection such as AIDS by methods well known in the art, an AV shunt or arterial bypass is attached to the patient. An extracorporeal peroxidizing module is attached to the AV shunt or arterial bypass. It has an inlet fluid connection from a pump which introduces hydrogen peroxide into the module which contains peroxidase or lipoxidase which in turn peroxidizes the plasma lipoproteins.

EXAMPLE 5

Once a patient is diagnosed or suspected as having a viral infection such as AIDS, a disease state characterized by diseased cells with an enhanced ability to take-up lipoproteins or an increased susceptibility to oxidized lipoproteins, by methods well known in the art, a supply of blood is secured. The blood supply source may be from the diseased patient a donor, a blood bank or any other compatible blood supply source. Blood from sources other than the diseased patient have the advantage of being from apparently healthy donors.

The lipoproteins of the blood supply are then oxidized by adding an oxidant to the blood, thus producing oxidized lipoproteins. A second approach to increasing the blood's level of oxidized lipoproteins involves adding oxidized lipoproteins to the blood. As a third approach, the first two approaches may be combined, that is an oxidant as well as the oxidized lipoproteins are added to the same blood supply.

When a blood supply other than the patient's is involved, the oxidized lipoprotein-containing blood may be stored until needed. When the patient's blood is used, it may be reintroduced to the patient at the most advantageous time for treatment.

Several additional and optional treatment steps may be combined with the above-described procedure. They are as follows.

The oxygen available in the blood may be further increased by adding elemental oxygen or perfluorocarbon fluosal to the blood.

The lipoprotein content of the blood could also be augmented by adding lipoproteins enriched with triglycerides, phospholipids or cholesterol esters.

This treatment approach appears to work best when the lipoproteins referred to are low density lipoproteins.

EXAMPLE 6

One embodiment of this invention involves providing a blood supply which may include the diseased patient's blood, a blood bank or any other compatible blood supply.

Heparinized blood 66 is added to the bottom of a container 68, shown in FIG. 5, the walls of which confine a source of an immobilized enzyme such as horseradish peroxidase coated beads 70. Hydrogen peroxide 72 is introduced to the bottom of the container resulting in the formation of oxidized lipoproteins 74 in the blood which exits from the top of the container. The oxidized lipoprotein-containing blood 74 is then introduced to the patient 76 when treatment of the disease state is desired.

This procedure may be further enhanced by introducing an oxidant to the blood prior to administering it to the patient.

The invention may be embodied in other specified forms without departing from the spirit or essential characteristics thereof. The present embodiments are therefore to be considered in all respects as illustrative and not restrictive the scope of the invention being indicated by the appended claims rather than by the foregoing description, and all changes which come within the meaning and range of equivalents of the claims are therefore intended to be embraced therein.

What is claimed is:

1. A method for treating virus infection in cells comprising selective killing of virus infected cells comprising exposing virus infected cells to an effective amount of an oxidized lipoprotein, while not substantially killing uninfected cells.

2. The method of claim 1 wherein the oxidized lipoprotein is formed using an oxidant selected from the group consisting of a flavin, riboflavin, an oxidase, a peroxidase, a lipoxidase or a peroxide.

3. A method for treating virus infections in cells with oxidized low density lipoproteins comprising:
   (a) providing a solution of low density lipoptoteins;
   (b) subjecting the low density lipoproteins solution to a peroixde in the presence of an enzyme catalyst capable of catalyzing the peroxidation of low density lipoproteins;
   (c) obtaining a carbon-13 nuclear magnetic resonance spectrum of the oxidized low density lipoprotein solution to determine the extent of lipid peroxidation measured by the 128/130 ppm ratio; and, (d) repeating steps (b) and (c) until a desired level of oxidized low density lipoprotein in a selectively toxic dose is reached;

(e) exposing the viral infected cells to the oxidized low density lipoprotein solution.

* * * * *

UNITED STATES PATENT AND TRADEMARK OFFICE
CERTIFICATE OF CORRECTION

PATENT NO. : 5,217,716

DATED : June 8, 1993

INVENTOR(S) : Eric T. Fossel, James E. Lyddy

Page 1 of 2

It is certified that error appears in the above-indentified patent and that said Letters Patent is hereby corrected as shown below:

Col. 1, line 29, after "exists" delete "o" and insert --on--;

Col. 2, line 51, after "as" insert --a--;

Col. 4, line 49, after "proteins" delete "ar" and insert --are--;

Col. 5, line 14, after "administered" insert --,--;

Col. 5, line 15, after "that" delete "ar" and insert --are--;

Col. 5, line 25, after "arranged" delete "o" and insert --on--;

Col. 5, line 26, after "hydrophilic" delete "properLies" and insert --properties--;

Col. 7, line 62, after "patient" insert --,--;

UNITED STATES PATENT AND TRADEMARK OFFICE
CERTIFICATE OF CORRECTION

PATENT NO. : 5,217,716

DATED : June 8, 1993

INVENTOR(S) : Eric T. Fossel, James E. Lyddy

It is certified that error appears in the above-indentified patent and that said Letters Patent is hereby corrected as shown below:

Col. 8, line 64, after "a" delete "peroixide" and insert --peroxide--;

Col. 10, line 2, after "reached;" insert --and--.

Signed and Sealed this

Fifteenth Day of March, 1994

Attest:

BRUCE LEHMAN

*Attesting Officer*     *Commissioner of Patents and Trademarks*